United States Patent [19]

Iimuro et al.

[11] Patent Number: 4,950,805

[45] Date of Patent: Aug. 21, 1990

[54] PROCESS FOR WASHING AND OBTAINING SOLIDS OF SLURRY

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 310,345

[22] Filed: Feb. 14, 1989

[30] Foreign Application Priority Data

Feb. 19, 1988 [JP] Japan .................................. 63-35121

[51] Int. Cl.$^5$ ...................... C07C 45/78; C07C 45/90; C07C 45/81
[52] U.S. Cl. ..................................... 568/724; 568/749
[58] Field of Search ................ 568/722, 724, 727, 728

[56] References Cited

U.S. PATENT DOCUMENTS

| | | | |
|---|---|---|---|
| 3,049,568 | 8/1962 | Apel et al. ........................... | 568/727 |
| 3,221,061 | 11/1965 | Grover et al. ...................... | 568/727 |
| 3,936,507 | 2/1976 | Ligorati et al. ..................... | 568/727 |
| 4,209,646 | 6/1980 | Gac et al. ............................ | 568/724 |
| 4,300,000 | 11/1981 | Reinitz ................................. | 568/724 |
| 4,408,087 | 10/1983 | Li .......................................... | 568/724 |
| 4,492,807 | 1/1985 | Aneja ................................... | 568/724 |
| 4,529,823 | 6/1985 | Mendiratta .......................... | 568/724 |
| 4,740,634 | 4/1988 | Gomes et al. ....................... | 568/724 |

FOREIGN PATENT DOCUMENTS

| | | | |
|---|---|---|---|
| 0110242 | 6/1984 | European Pat. Off. ............ | 568/724 |
| 11-23335 | 12/1936 | Japan ................................... | 568/724 |
| 59-62543 | 4/1984 | Japan ................................... | 568/727 |

*Primary Examiner*—Werren B. Lone
*Attorney, Agent, or Firm*—Burns, Doane, Swecker & Mathis

[57] ABSTRACT

A process for washing and obtaining solids of a slurry comprises feeding a slurry containing the adduct of bisphenol A with phenol crystallized from a phenol solution of bisphenol A to a first solid-liquid separator to separate solids from the slurry, transferring the solids separated by the first solid-liquid separator to an agitation tank in which the solids are reslurried, feeding the slurry obtained in the agitation tank to a second solid-liquid separator, said second solid-liquid separator being intended to obtain the solids from the slurry discharged from the agitation tank, and permitting the admission of a washing solvent to wash the solids, and permitting the filtrate and washings to be recovered independently, feeding the washing solvent to the second solid-liquid separator, feeding all of the washings from the second solid-liquid separator to the agitation tank, feeding a part of the filtrate from the second solid-liquid separator to the agitation tank, and discharging the remainder of the filtrate from the system. The process makes it possible to produce a high-purity adduct of bisphenol A with phenol and hence high-purity bisphenol A.

5 Claims, 1 Drawing Sheet

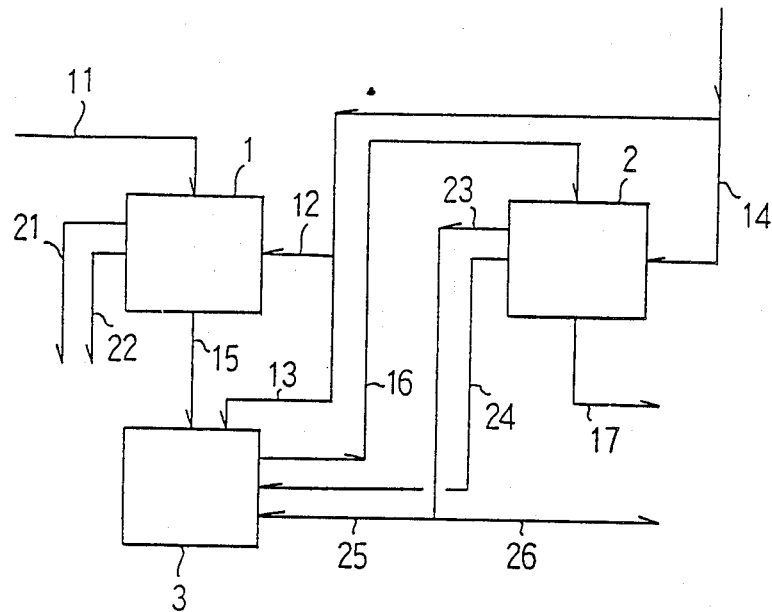

PROCESS FOR WASHING AND OBTAINING SOLIDS OF SLURRY

BACKGROUND OF THE INVENTION

The present invention relates to a process for washing and obtaining solids of a slurry. More particularly, it relates to a process for washing and obtaining the adduct of bisphenol A with phenol, said process being used for the production of high-purity bisphenol A.

Bisphenol A is used as a raw material for polycarbonate resins and epoxy resins. There is an increasing demand for colorless and high-purity bisphenol A (superior in quality to the conventional ones) which meets the requirements of polycarbonate resins for optical applications.

Bisphenol A is produced by reacting acetone with excess phenol in the presence of an acid catalyst and an optical co-catalyst such as a sulfur compound. The product mixture contains, in addition to bisphenol A, the catalyst, unreacted acetone, unreacted phenol, water, and by-products.

The by-products contain as major components 2-(2-hydroxyphenyl)-2-(4-hydroxyphenyl)propane (referred to as o,p'-isomer hereinafter) and Dianin's compound. Minor components include trisphenols, polyphenols, and coloring substances. They have adverse effects on the performance of the resins produced from such bisphenol A.

There have been proposed many processes for removing these impurities from such bisphenol A and obtaining high-purity bisphenol A.

One way of obtaining high-purity bisphenol A from the product mixture comprises removing the catalyst, unreacted acetone, water, and a small amount of phenol from the product mixture by vacuum distillation, cooling the residual liquid mixture, thereby causing bisphenol A to crystallize out in the form of an adduct with phenol, separating the resulting crystals from the mother liquor containing by-products, and removing phenol from the adduct, thereby obtaining bisphenol A.

According to another way, high-purity bisphenol A is obtained by recrystallizing from a solution of crude bisphenol A.

The removal of phenol from the adduct of bisphenol A with phenol may be accomplished by distillation, extraction, steam stripping, or the like. According to a process disclosed in U.S. Pat. No. 3,936,507 and Japanese Patent Publication No. 42790/1977, the adduct is vaporized for 0.1 to 30 minutes under reduced pressure at 180° C. or above for separating and condensing bisphenol A. According to a process disclosed in Japanese Patent Publication No. 23335/1961, the adduct is heated to 50° C. or above in a solvent having a boiling point higher than 50° C. so that the phenol moiety alone is dissolved in the solvent.

The above-mentioned processes give bisphenol A that can be used as a raw material of general-purpose epoxy resins for example. However, this bisphenol A does not have a high purity satisfactory for use as a raw material of polycarbonate resins and other linear polymers. It needs further purification by recrystallizing from a hot aqueous solution (as disclosed in Japanese Patent Laid-open No. 62543/1984) or washing with a solvent (as disclosed in U.S. Pat. No. 4,492,807 and Japanese Patent Laid-open No. 231033/1984).

Heretofore, it has been believed that the above-mentioned post treatment is necessary to remove these impurities completely from bisphenol A because the adduct crystals themselves contain these impurities and hence they give bisphenol A of low purity after they are freed of phenol. However, we found that the adduct crystals of high purity do not necessarily give bisphenol A which has a satisfactory hue. Presumably, this is attributable to trace amounts of the mother liquor remaining on the adduct crystals separated from the mother liquor.

The adduct crystals may be freed of the mother liquor by washing them with phenol continuously or intermittently in the separator or by reslurrying them in fresh phenol after being discharged from the separator. The former method does not perform complete washing, and the latter method needs at least as much phenol as the adduct crystals for transferring the slurry to the subsequent separation step.

Examples of washing processes are disclosed in U.S. Pat. No. 3,049,568 and 3,221,061 and Japanese Patent Publication Nos. 981/1964 and 4454/1968. According to these processes, the centrifuged adduct crystals are suspended again in as much phenol as 70 wt% of the adduct crystals, and the resulting slurry is fed to the separator again and washed again with as much phenol as 20 wt% of the crystals.

This process has a disadvantage of decreasing the yield of the adduct crystals because bisphenol A is somewhat soluble in phenol.

SUMMARY OF THE INVENTION

It is an object of the present invention to provide a process for washing and obtaining solids of a slurry containing crystals of the adduct of bisphenol A with phenol which have been crystallized from a phenol solution of bisphenol A containing by-products and impurities, without using a large amount of water or solvent.

As a result of our extensive studies, we found that the aforesaid object is achieved by using two solid-liquid separators and one agitation tank for the slurry. The present invention was completed on the basis of this finding.

In accordance with the present invention, there is provided a process for washing and obtaining solids of a slurry which comprises feeding a slurry containing the adduct of bisphenol A with phenol crystallized from a phenol solution of bisphenol A to a first solid-liquid separator to separate solids from the slurry, transferring the solids separated by the first solid-liquid separator to an agitation tank in which the solids are reslurried, feeding the slurry obtained in the agitation tank to a second solid-liquid separator, said second solid-liquid separator being intended to obtain the solids from the slurry discharged from the agitation tank, and permitting the admission of a washing solvent to wash the solids, and permitting the filtrate and washings to be recovered independently, feeding the washing solvent to the second solid-liquid separator, feeding all of the washings from the second solid-liquid separator to the agitation tank, feeding a part of the filtrate from the second solid-liquid separator to the agitation tank, and discharging the remainder of the filtrate from the system.

BRIEF DESCRIPTION OF THE DRAWINGS

The accompanying drawing is a flowsheet showing an embodiment of the process of the present invention for washing and obtaining solids of a slurry.

DETAILED DESCRIPTION OF THE INVENTION

The process of the present invention may be applied to a slurry containing crystals of the adduct of bisphenol A with phenol. The slurry may be one which is obtained directly from the product mixture, or one which is obtained by concentrating the filtrate obtained in the crystallization step to separate the adduct from the product mixture. The slurry may also be one which is obtained by dissolving crude bisphenol A in phenol with heating and then cooling the solution for recrystallization.

The slurry will be obtained by reacting phenol with acetone in the presence of hydrochloric acid catalyst, freeing the product mixture of hydrochloric acid, water, and a small amount of phenol by distillation, and finally cooling the residue. The slurry will also be obtained by cooling directly the effluent from a fixed bed reactor of cation-exchange resin. Furthermore, the slurry will be obtained by adding water to a mixture of bisphenol A and phenol and evaporating the water, thereby cooling the mixture for crystallizing the adduct.

According to the process of the present invention, the mother liquor containing 5 to 20 wt% of bisphenol A and by-products is almost separated by a first solid-liquid separator. The separated mother liquor (filtrate) may be recycled to the reactor as a raw material or fed to a separate step for recovering bisphenol A. If necessary, the adduct crystals obtained in the first solid-liquid separator may be washed with a washing solvent which is phenol or water-containing phenol. The washing of the adduct crystals may be accomplished continuously in the filter or separator to separate the adduct crystals, after removing the mother liquor. It is also possible to perform separation and washing alternately.

The first solid-liquid separator discharges the adduct crystals which carry a small amount of the mother liquor. The adduct crystals are reslurried in a separate tank. The resulting slurry is fed to a second solid-liquid separator for separation and washing.

The washings from the second solid-liquid separator are all charged into the agitation tank. The filtrate from the second solid-liquid separator is partly discharged from the system, and the remainder is used as the dispersing medium for reslurrying. The amount of the filtrate to be discharged is balanced with the amount of washing solvent to be added (the washing phenol fed to the agitation tank and the washing phenol fed to the second solid-liquid separator). Since the amount of washing solvent to be added is 10 to 40 wt% of the amount of the adduct from the first solid-liquid separator, the amount of the adduct which will dissolve in the replenished washing solvent is kept minimal. This leads to an increased yield of crystals.

When the separated solids are reslurried, the slurry concentration can be changed as desired by increasing or decreasing the amount of the filtrate recirculated from the second solid-liquid separator. The solid content at the time of reslurrying should preferably be 30 to 50 wt% for the adequate efficiency of recycling and the ease of transfer.

The washing phenol (or washing solvent) that can be used in the process of the present invention may be fresh phenol; but it is desirable to use the phenol which is obtained as one product when the adduct of bisphenol A with phenol is decomposed for recovering bisphenol A. The washing phenol is used in an amount up to about 60 wt% of the adduct crystals. The washing phenol in an excess amount must be discharged from the system, because phenol becomes superfluous in the whole production system for bisphenol A.

The washing solvent should be added at as low a temperature as possible above its freezing point so as to avoid excessive dissolution of the adduct crystals. The preferred temperature ranges from 40 to 45° C. in the case where it is pure phenol, and ranges from 35° to 45° C. in the case where it is phenol containing 5 wt% of water.

The thus-obtained adduct crystals are almost completely free of impurities (in both crystals and liquids carried by crystals). Therefore, upon removing phenol from the adduct crystals in the usual way, they give bisphenol A that can be commercialized as such or after further purification and molding.

The filtrate from the second solid-liquid separator may be recycled to the reaction or crystallization step for recovering a small amount of bisphenol A which is inevitably dissolved in it.

The process of the present invention will be explained with reference to the flowsheet shown in the accompanying drawing.

A feedstock slurry 11, which contains crystals of the adduct of bisphenol A with phenol obtained in the crystallization step and also bisphenol A, phenol, water, and by-products obtained in the reaction for producing bisphenol A, is fed to a first solid-liquid separator 1, in which the mother liquor in the slurry is mostly separated from solids and discharged as the filtrate 21. Then, the separated adduct crystals are washed with a small amount of washing phenol 12, and the washings 22 are discharged. The washed adduct crystals 15 are fed to a reslurrying tank 3 in which the washed adduct crystals 15 are reslurried with a part 25 of the filtrate 23 from a second solid-liquid separator 2, the washings 24, and optionally a small amount of washing phenol 13. The resulting slurry 16 is fed to the second solid-liquid separator 2 in which solids are separated and washed as in the case of the first solid-liquid separator. A part 25 of the filtrate 23 from the second solid-liquid separator 2 is used for reslurrying, and the remainder 26 is recycled to the reaction step or crystallizing step. The washings 24 from the second solid-liquid separator are all used for reslurrying. The adduct crystals 17 discharged from the second solid-liquid separator 2 are freed of phenol in the usual way. Thus there is obtained the desired product.

EXAMPLES

The invention will be described in more detail with reference to the following examples, in which "%" means "wt%", unless otherwise indicated.

EXAMPLE 1

40 Kg/hr of water was added to 400 kg/hr of a mixture composed of bisphenol A, phenol, and impurities and the mixture was cooled by evaporating the water under reduced pressure to obtain a slurry. This slurry was composed of 45% of solids and the remaining liquid phase contained 12% of bisphenol A, 4% of o,p'-isomer, 2% of Dianin's compound, 3.5% of water, phenol, and trace amounts of by-products. As shown in the accompanying drawing, the slurry was continuously fed to a first solid-liquid separator (Guinard type centrifugal separator, manufactured by IHI). After separating the mother liquor, the solids were washed in the first solid-liquid separator with phenol which was fed continuously at a flow rate of 10 kg/hr. The washed crystals contained 67% of bisphenol A, 0.1% of o,p'-isomer, and 0.05% of Dianin's compound. The crystals were continuously fed to a reslurrying tank. At the same time, a part of the filtrate and all of the washings both from a second solid-liquid separator (Guinard type centrifugal separator, manufactured by IHI) were fed to the reslurrying tank. The slurry containing 40% of solids was fed to the second solid-liquid separator. To the second solid-liquid separator was also fed washing phenol at a flow rate of 20 kg/hr. (This washing phenol was obtained by decomposing the adduct.) After the washing, the washings were all fed to the reslurrying tank. The crystals obtained from the second solid-liquid separator contained 69.9% of bisphenol A and trace amounts of o,p'-isomer (0.02%) and Dianin's compound (0.005%).

The thus-obtained adduct was melted by heating at 120° C. and fed to a distillation column at a flow rate of 150 kg/hr. A large part of phenol was distilled away for recovering at 15 Torr and 170° C. The bisphenol A discharged from the bottom of the distillation column was completely freed of residual phenol by steam stripping. Thus there was obtained the desired bisphenol A. The resulting bisphenol gave a Hazen color of 10 APHA and had a purity high enough for use as a raw material for the preparation of optical polycarbonate resins.

According to the process of the present invention, it is possible to effectively wash and obtain solids of a slurry. This process can be applied to obtain a high-purity adduct of bisphenol A with phenol. After removing phenol, there is obtained high-purity bisphenol A which can be used as such (without further purification) for polycarbonate resins etc.

What is claimed is:

1. A process for washing and obtaining solids of a slurry which comprises feeding a slurry containing the adduct of bisphenol A with phenol crystallized from a phenol solution fo bisphenol A to a first solid-liquid separator to separate solids from the slurry, transferring the solids separated by the first solid-liquid separator to an agitation tank in which the solids are reslurried, feeding the slurry obtained in the agitation tank to a second solid-liquid separator, said second solid-liquid separator being intended to obtian the solids from the slurry discharged from the agitation tank, and permitting the admission of a washing solvent consisting of phenol or water-containing phenol at a temperature of 35° to 45° C. to wash the solids, and permitting the filtrate and washings to be recovered independently, feeding the washing solvent to the second solid-liquid separator, feeding all of the washings from the second solid-liquid separator, feeding all of the washings from the second solid-liquid separator to the agitation tank, feeding a part of the filtrate from the second solid-liquid separator to the agitation tank, and discharging the remainder of the filtrate from the system.

2. A process as claimed in claim 1, wherein the washing solvent is phenol at a temperature of 40° to 45° C.

3. A process as claimed in claim 1, wherein the washing solvent is water-containing phenol at a temperature of 35° to 45° C.

4. A process as claimed in claim 1, wherein the slurry formed in the agitation tank contains 30 to 50 wt% of solids.

5. A process as claimed in claim 1, wherein the washing solvent is used in a total amount which is less than 60 wt% of the total amount of the adduct crystals to be washed.

* * * * *